(12) United States Patent
Miller et al.

(10) Patent No.: US 12,702,813 B2
(45) Date of Patent: Aug. 11, 2026

(54) X-BAR STOPCOCK DEVICE FOR PULMONARY ARTERY CATHETERIZATION

(71) Applicant: REGENTS OF THE UNIVERSITY OF MICHIGAN, Ann Arbor, MI (US)

(72) Inventors: Mark Miller, Ann Arbor, MI (US); Tracy Birchmeier, Ann Arbor, MI (US); Bree Susalla, Ann Arbor, MI (US); Yuru Chen, Ann Arbor, MI (US); Rayna Berris, Ann Arbor, MI (US); Cara Spencer, Ann Arbor, MI (US); Caroline Schmiedeler, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 745 days.

(21) Appl. No.: 18/082,968

(22) Filed: Dec. 16, 2022

(65) Prior Publication Data

US 2023/0191104 A1 Jun. 22, 2023

Related U.S. Application Data

(60) Provisional application No. 63/291,184, filed on Dec. 17, 2021.

(51) Int. Cl.
*A61M 39/22* (2006.01)
*A61B 5/153* (2006.01)

(52) U.S. Cl.
CPC .......... *A61M 39/223* (2013.01); *A61B 5/153* (2013.01); *A61M 2039/229* (2013.01)

(58) Field of Classification Search
CPC .......... A61M 2039/229; A61M 39/223; A61M 5/1408
See application file for complete search history.

(56) References Cited

U.S. PATENT DOCUMENTS

| | | | | |
|---|---|---|---|---|
| 4,949,723 | A * | 8/1990 | Wallace | A61B 5/021 600/561 |
| 2010/0030074 | A1 * | 2/2010 | Imai | A61M 39/10 366/132 |
| 2010/0312184 | A1 * | 12/2010 | Guzman | A61M 5/14212 604/122 |
| 2014/0196792 | A1 * | 7/2014 | Torres-Leon | A61M 39/223 137/1 |
| 2023/0284893 | A1 * | 9/2023 | Farnam | A61B 1/307 |
| 2024/0084937 | A1 * | 3/2024 | Yuen | F16L 29/007 |

* cited by examiner

*Primary Examiner* — Courtney Fredrickson
(74) *Attorney, Agent, or Firm* — MARSHALL, GERSTEIN & BORUN LLP

(57) ABSTRACT

A unified X-bar stopcock, including a bidirectional stopcock having a first port, second port, third port, and fourth port; and a three-way stopcock having a fifth port, sixth port, and seventh port. The bidirectional stopcock is fluidly coupled to the three-way stopcock via the first port and the fifth port. A method of using the X-bar stopcock includes providing a Swan-Ganz catheter, an X-bar stopcock, a transducer, a monitor, and at least one bag of saline. The method includes connecting the X-bar stopcock to at least two lumens of the Swan-Ganz catheter. The method additionally includes connecting at least one port of the X-bar stopcock to the transducer connected to the monitor, connecting at least one port of the X-bar stopcock to the bag of saline, and connecting the transducer to the bag of saline. The unified X-bar stopcock may also include a protective case.

12 Claims, 9 Drawing Sheets

X-BAR STOPCOCK DEVICE FOR PULMONARY ARTERY CATHETERIZATION

CROSS REFERENCE TO RELATED APPLICATION

Priority is claimed to U.S. Provisional Patent Application No. 63/291,184, filed Dec. 17, 2021, and the entire contents thereof are hereby incorporated herein by reference.

FIELD OF THE DISCLOSURE

The present disclosure relates generally to pulmonary artery catheterization devices and, more particularly, to a bidirectional stopcock used in pulmonary artery catheterization.

BACKGROUND

Cardiovascular disease is highly prevalent and on the rise in the United States and throughout the world. Pulmonary artery catheterization can be used for treatment and diagnosis for a wide variety of cardiovascular and other medical conditions. For example, every year approximately 50,000 patients suffering heart failure receive pulmonary artery catheters for diagnosis and/or treatment. In other examples, pulmonary artery catheterization can be used to diagnose and/or treat shock, pulmonary edema, heart attack, kidney failure, sepsis, high blood pressure, and ventilator management.

Pulmonary artery catheterization involves inserting a catheter into a blood vessel, for example, the right internal jugular. In some examples, the catheter may include a Swan-Ganz catheter having several lumens. After the catheter is properly disposed in the patient, a medical professional will connect each of the several lumens of the catheter, configured at the bedside of a patient or, often, in a catheter lab, to a valve system and a monitor. The attached valve system can be used to selectively administer fluids, measure blood pressure, and draw blood for testing.

SUMMARY

A unified X-bar stopcock includes a bidirectional stopcock having a first port, second port, third port, and fourth port; and a three-way stopcock having a fifth port, sixth port, and seventh port. The bidirectional stopcock is fluidly coupled to the three-way stopcock via the first port and the fifth port. At least one of the first, second, third, fourth, fifth, sixth, and seventh ports comprises a luer lock.

The unified X-bar stopcock may additionally include a bidirectional handle element having a first position and a second position. When the bidirectional handle is in the first position the first port and second port are in fluid communication and the third port and the fourth port are in fluid communication. Alternatively, when the bidirectional valve is in the second position the first port and fourth port are in fluid communication and the second port and third port are in fluid communication. In some embodiments, the second port and the fourth port are color coded. Further, the second port may be coded with a first color and the fourth port may be color coded with a second color, the first color being different from the second color. The unified X-bar stopcock additionally includes a three-way handle element. The bidirectional stopcock is secured to the three-way stopcock.

The unified X-bar stopcock may also include a protective case. In some examples, the protective case is transparent, while in other examples, the protective case is lightly tinted. Additionally, at least one of the bidirectional stopcock and three-way stopcock are secured to the case. The protective case includes a first aperture corresponding to the bidirectional handle element when the bidirectional stopcock is disposed in the protective case and a second aperture corresponding to the three-way handle element when the three-way stopcock is disposed in the case. The protective case includes at least five orifices corresponding, respectively, to the second port, third port, fourth port, sixth port, and seventh port.

A method of using an X-bar stopcock includes providing a Swan-Ganz catheter, an X-bar stopcock, a transducer, a monitor, and at least one bag of saline; and connecting the X-bar stopcock to at least two lumens of the Swan-Ganz catheter. The method additionally includes connecting at least one port of the X-bar stopcock to the transducer connected to the monitor, connecting at least one port of the X-bar stopcock to the bag of saline, and connecting the transducer to the bag of saline. The X-bar stopcock includes a bidirectional stopcock and a three-way stopcock.

Using the X-bar stopcock includes actuating the bidirectional stopcock between a first position and a second position and actuating the three-way stopcock between a first position and a second position. The method of using the X-bar stopcock includes monitoring a pulmonary artery pressure when the bidirectional stopcock is in the first position and the three-way stopcock is in the second position. Alternatively, the X-bar stopcock can monitor a right atrium pressure when the bidirectional stopcock is in the second position and the three-way stopcock is in the second position. Furthermore, after providing a syringe and attaching a syringe to a sixth port of the three-way stopcock, the X-bar stopcock can be used to draw a blood sample via the syringe when the bidirectional stopcock is in the second position and the three-way stopcock is disposed in the first position.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except what may be explicitly delineated in the corresponding written description. None of the drawings are necessarily to scale.

Figure 1:
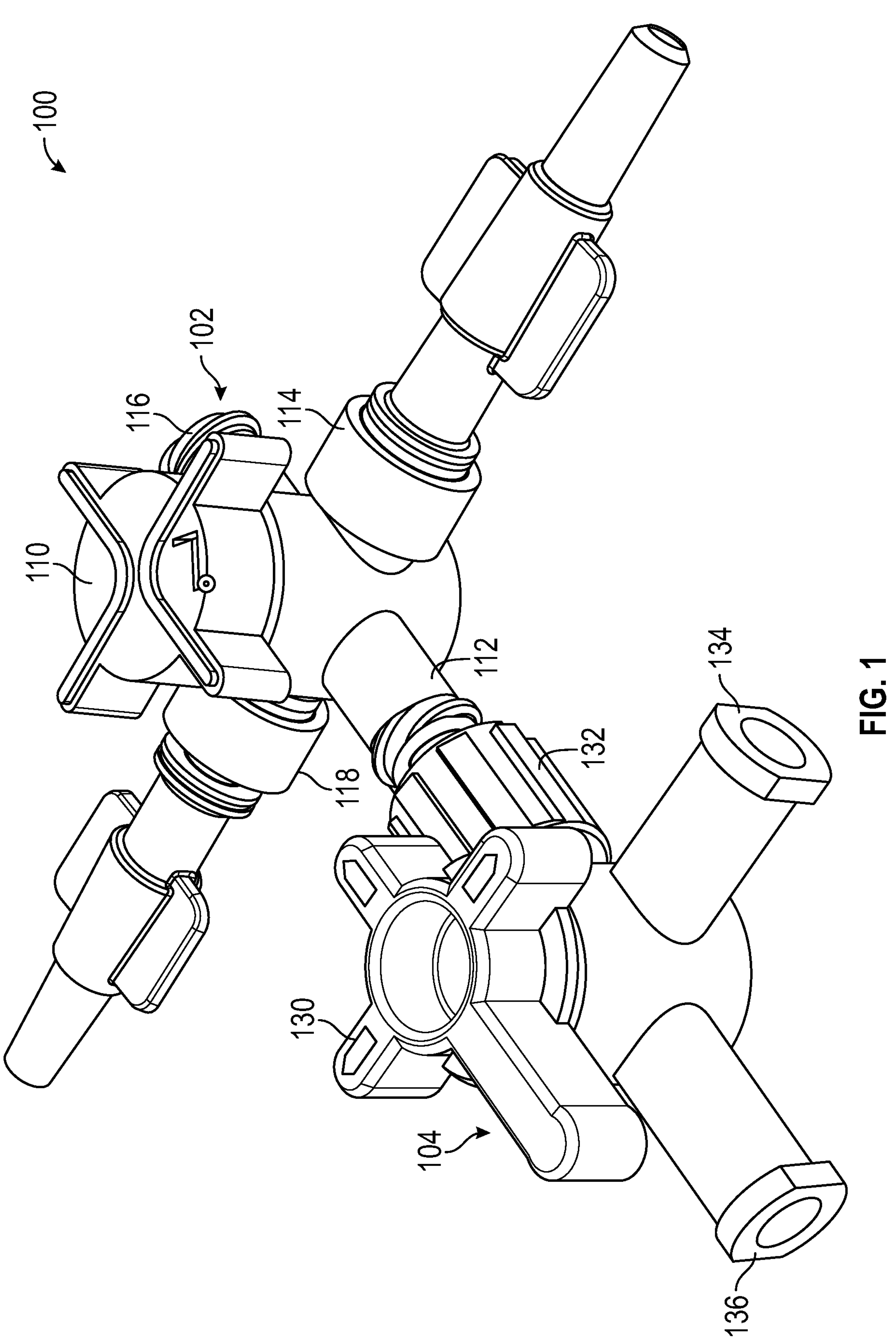
FIG. 1 is a perspective view of an X-bar stopcock for pulmonary artery catheterization in accordance with the teachings of this disclosure.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Medical professionals often utilize a pulmonary artery catheterization (PAC) to diagnose and treat a variety of cardiac medical conditions. To perform a PAC, a medical professional may utilize a Swan-Ganz catheter, having a plurality of lumens. Each of the lumens can be used to monitor blood pressure, administer fluids, and/or draw blood. As a result, a medical professional can detect changes in blood pressure, administer medication, and sample blood to perform any of a variety of tests. Additionally, the lumens are normally attached to a combination of directional valves to direct fluids through the lumens (e.g., blood, saline, medication).

Typically, the combination of directional valves connected to the Swan-Ganz catheter may comprise several three-way valves and various fluid connections. The combination of valves may comprise an H-bar or I-bar configuration of valves. However, these configurations of valves can result in incorrect waveform readings, blood loss, and/or infections. For example, any of the several fluid connections may be loosened and separate such that a patient begins to lose blood. In such an example, to mitigate a potentially dangerous condition, the fluid connections may be reattached in a non-sterile manner that can result in infection. Further, such complications or confusions in actuating the various valves may result in improper readings that can result in misdiagnosis and less than ideal treatments.

In contrast to the previous H-bar and I-bar configurations, the present disclosure involves an X-bar stopcock having a one-piece arrangement of valves and connectors. As used herein, the meaning of the term "unified" includes being formed as a one-piece arrangement. The X-bar stopcock includes a bidirectional valve and a three-way valve. As a result, the X-bar has a fewer connections than the previous H-bar and I-bar designs. Thus, there is reduced complication in constructing the configuration of valves and fluid connections. In some examples, the X-bar stopcock has a two-piece arrangement (e.g., a non-unified arrangement).

The X-bar stopcock of the present disclosure provides several benefits over conventional configurations. One benefit of the new X-bar stopcock, is that the new device is easier to set up during a pulmonary artery catheterization procedure. Additionally, the device is smaller and more lightweight than the previous configurations, making the X-bar stopcock more comfortable for the patient, appear less cluttered, and less prone to potential entanglement. Also, because there a fewer ports and fluid connections, there is reduced chance of any disconnections resulting in blood loss or incorrect waveform readings. Because there are fewer disconnections, the chance of a central line infection is also significantly reduced.

In some embodiments, the X-bar stopcock additionally comprises a protective case. The protective case secures the X-bar stopcock and further reduces disconnection between the X-bar stopcock and the lumens of a Swan-Ganz catheter. Additionally, the X-bar stopcock can be positioned to rest on the patients shoulder, preferably the right shoulder. The X-bar stopcock, disposed in a protective, preferably transparent, case, is often more comfortable for the patient and has smoother sides and edges to reduce catching on the patients other wires and/or tubing.

FIG. 1 is an example X-bar stopcock 100 for a PAC in accordance with the teachings of this disclosure. As shown, the X-bar stopcock 100 includes a bidirectional stopcock 102 and a three-way stopcock 104. In some examples, the X-bar stopcock is a single piece device. As used herein, the meaning of the term "unified" covers apparatus made as a single piece.

Figure 2:
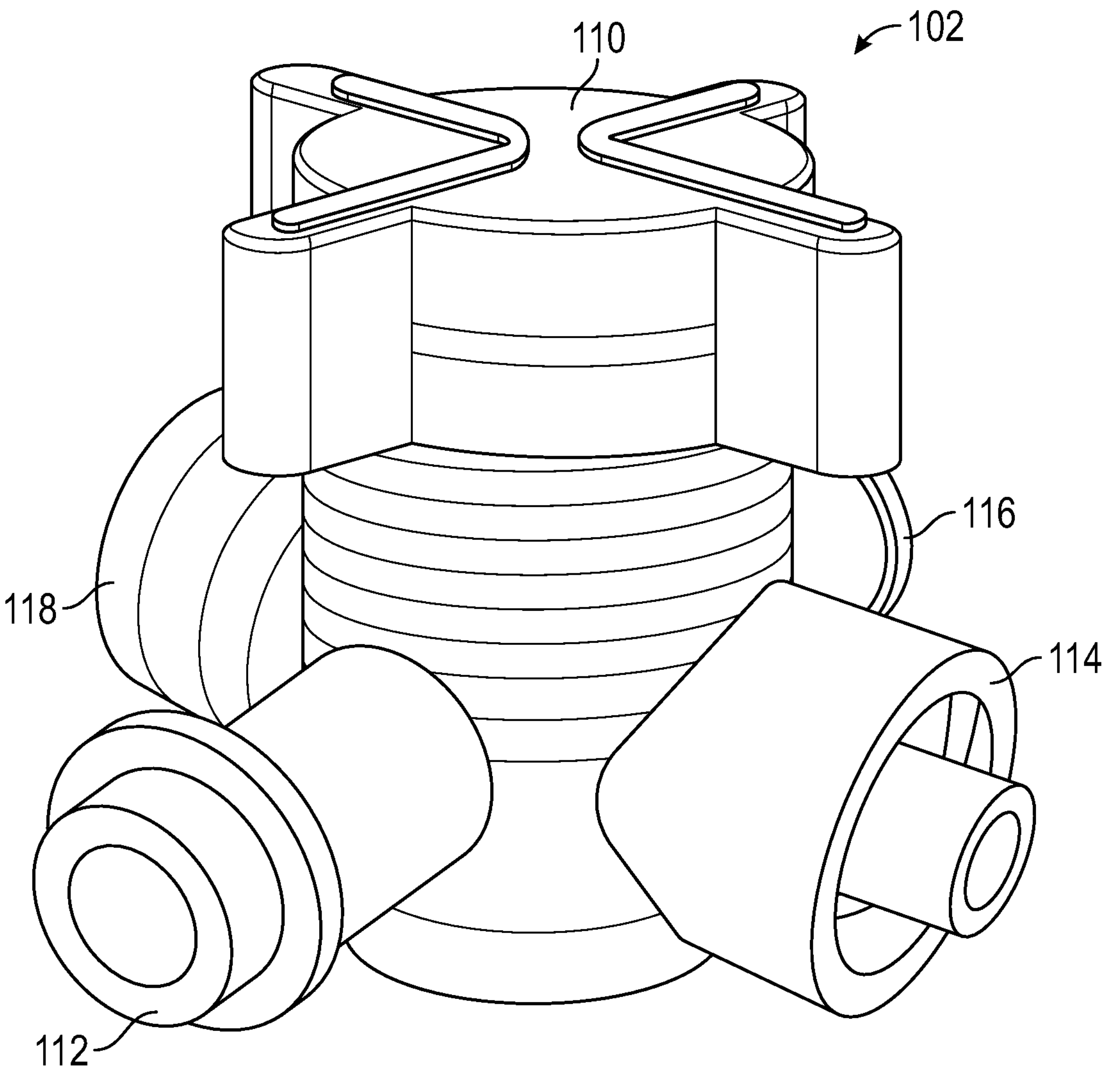
FIG. 2 is a perspective view of the bidirectional stopcock of the X-bar.
Figure 3A:
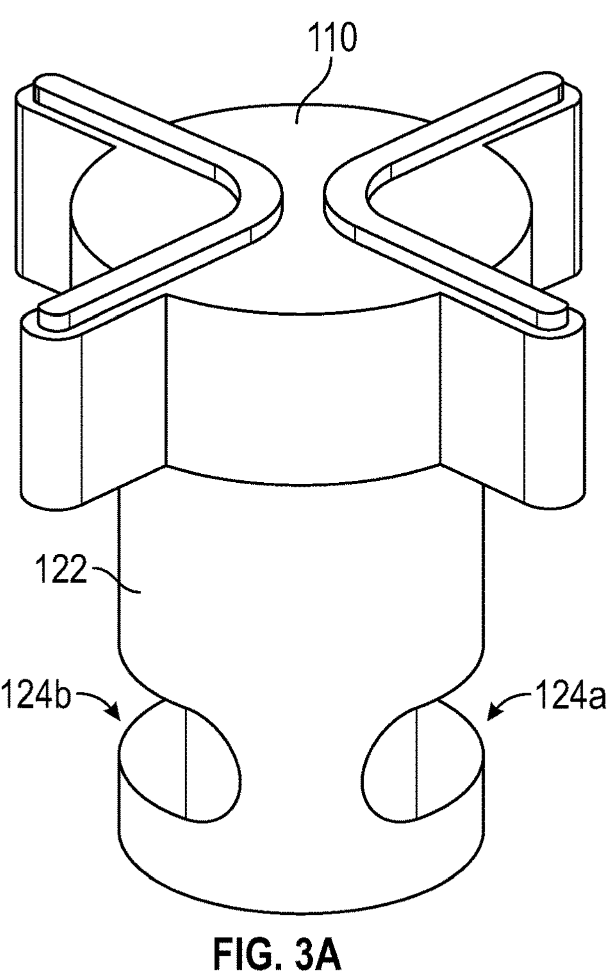
FIG. 3*a* is a first perspective view of a bidirectional handle element of the bidirectional stopcock.
Figure 3B:
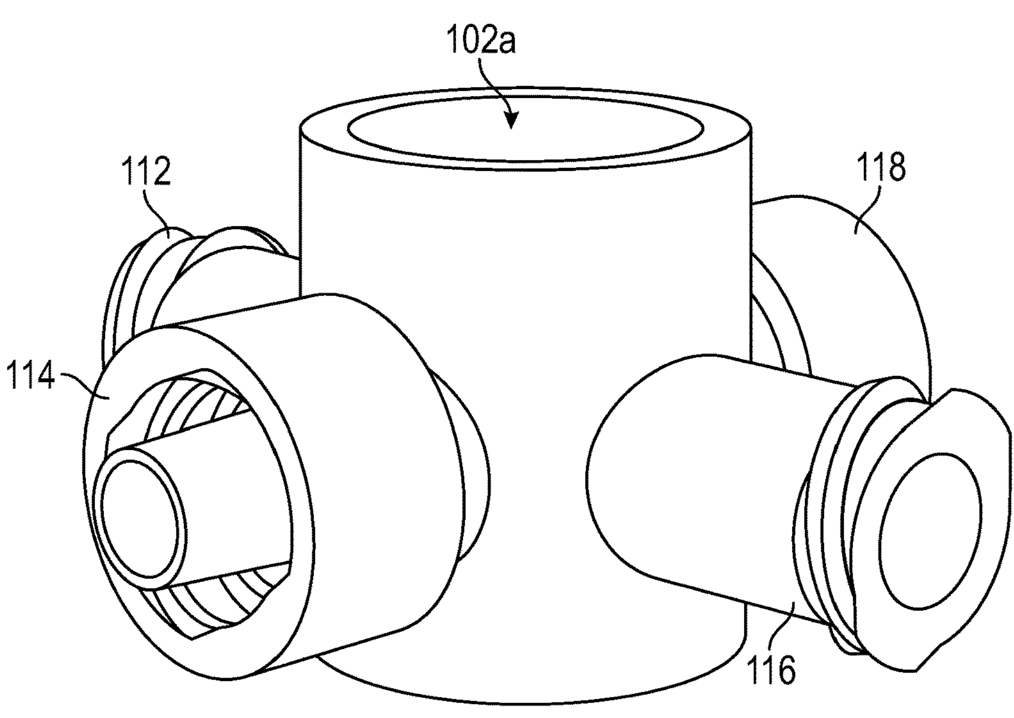
FIG. 3*b* is a second perspective view of a bidirectional stopcock body of the bidirectional stopcock.

The bidirectional stopcock 102 (shown in greater detail in FIGS. 2, 3*a*, and 3*b*) includes a bidirectional handle element 110 and a plurality of ports. The bidirectional stopcock 102 includes a first port 112, a second port 114, a third port 116, and a fourth port 118. As shown in FIG. 3*a*, the bidirectional handle element 110 includes a cylindrical body 122. The cylindrical body 122 of the bidirectional handle element 110 includes a first channel 124*a* and a second channel 124*b*. As shown, the first channel 124*a* and the second channel 124*b* are open channels, however in other examples, the first and second channels 124*a*, 124*b* are pipe channels. The bidirectional handle element 110 can pivot in the bidirectional stopcock 102 between a first position and a second position.

Returning to FIG. 1, the bidirectional stopcock 102 is illustrated in the first position. In the first position, the first port 112 is in fluid communication with the second port 114 while the third port 116 is in fluid communication with the fourth port 118. When the bidirectional handle element 110 is rotated 90 degrees (90°) or 270 degrees (270°), the bidirectional handle element is in the second position. In the second position, the first port 112 is in fluid communication with the fourth port 118 and the second port 114 is in fluid communication with the third port 116.

Figure 4:
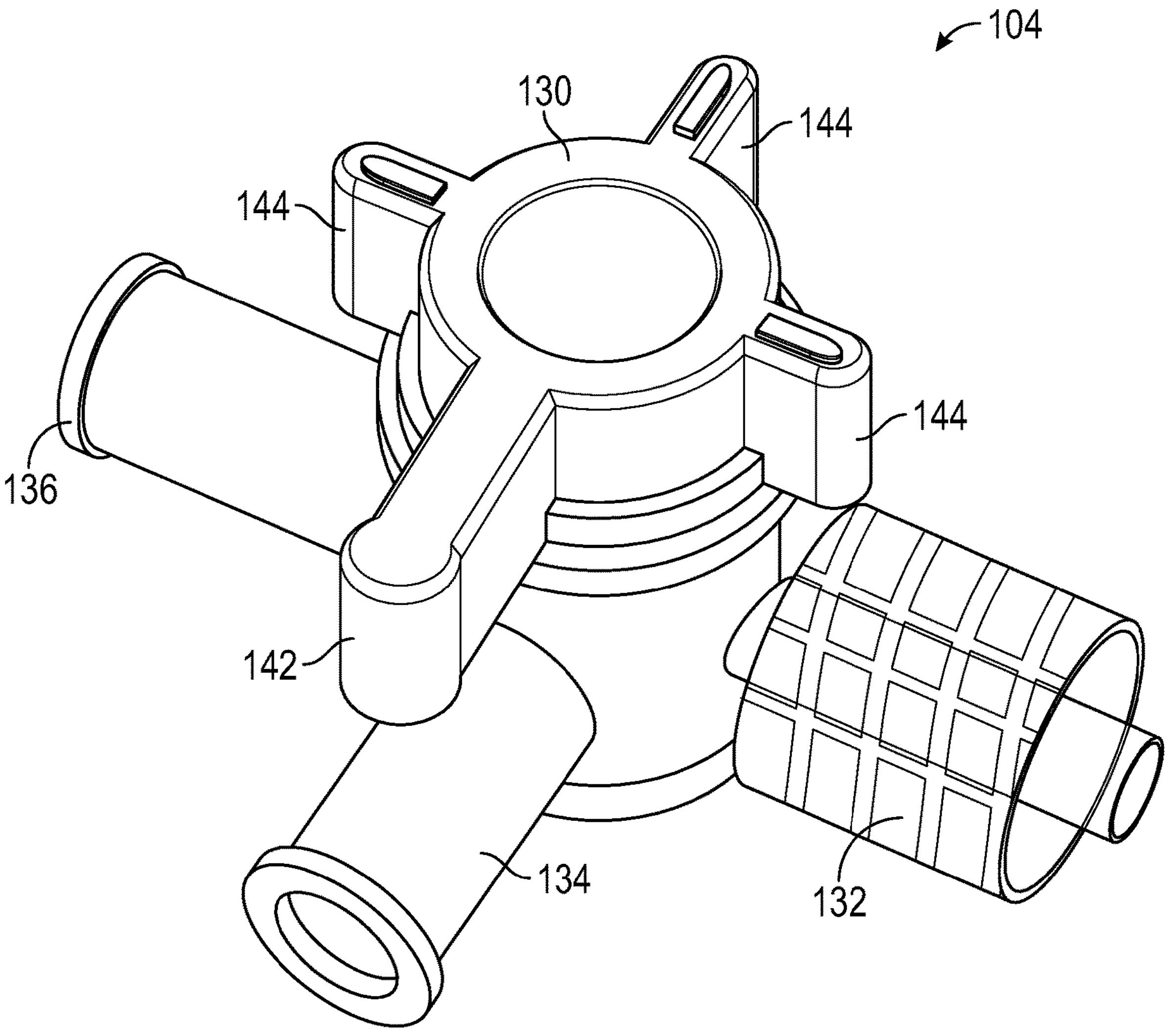
FIG. 4 is a perspective view of the three-way stopcock of the X-bar.

The three-way stopcock 104 (shown in greater detail in FIG. 4) includes a three-way handle element 130, a fifth port 132, sixth port 134, and a seventh port 136. As illustrated, the fifth port 132 is opposite the seventh port 136 and perpendicular to the sixth port 124. The three-way handle element 130 rotates relative to the three-way stopcock 104. The three-way handle element 130 is configured to fluidly connect two or three ports. As illustrated in FIGS. 1 and 4, the three-way handle element 130 includes an off indicator 142 and three flow path indicators 144. As illustrated in FIG. 1, the three-way handle element 130 is in a first position such that the off indicator 142 is disposed adjacent the seventh port 136. As a result, in the first position the fifth port 132 is in fluid communication with only the sixth port 134. In contrast, as illustrated in FIG. 4, the three-way handle element 130 is in a second position such that the off indicator 142 is disposed adjacent the sixth port 134. As a result, in the second position the fifth port 132 is in fluid communication with the seventh port 136.

Returning to FIG. 1, the bi-directional stopcock 102 is in fluid communication with the three-way stopcock 104. The first port 112 of the bi-directional stopcock 102 is secured to the fifth port 132 of the three-way stopcock. Further, as both the bi-directional handle element 110 and the three-way handle element 130 are in the first position, the sixth port 134 is in fluid communication with the second port 112. By actuating either or both the bi-directional handle element 110 or the three-way handle element 130, the second port 114 and the fourth port 118 can be selectively brought into fluid communication with the sixth port 134 and/or the seventh port 136.

Figure 5:
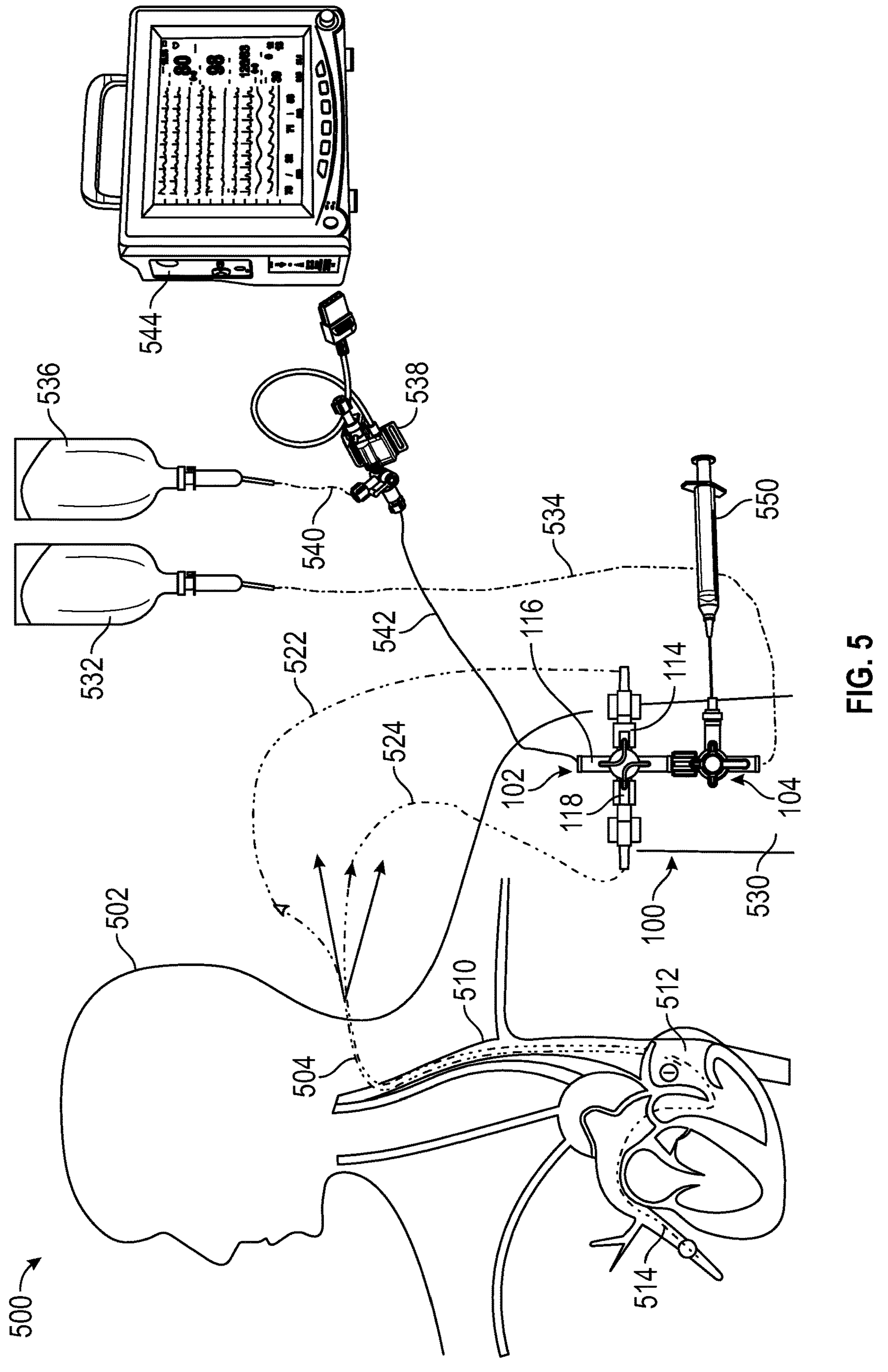
FIG. 5 is a semi-schematic and semi-anatomic diagram of the X-bar stopcock used in connection with a pulmonary artery catheterization procedure.

FIG. 5 is a semi-schematic, semi-anatomic diagram 500 of the X-bar stopcock 100 used in a PAC procedure of a patient 502. As illustrated, a Swan-Ganz catheter 504 has been inserted into a right jugular 506 of the patient 502. The Swan-Ganz catheter 504 enters into the right jugular 510, passes through the right atrium 512, and passes into the pulmonary artery 514. The blue lumen 522 is disposed in the right atrium and the yellow lumen 524 is disposed in the pulmonary artery 514. As shown, the blue lumen 522 is in fluid communication with the second port 114 and the yellow lumen 524 is in fluid communication with the fourth port 118.

In the illustrated example of FIG. 5, the X-bar stopcock 100 is placed on the right shoulder 530 of the patient 502. Securing the X-bar stopcock may vary by hospital, but may be secured to the patient via medical tape, elastic, clips, etc. The X-bar stopcock 100 can be releasably secured to the right shoulder 530. As the patient 502 may need to use the X-bar stopcock 100 for extended periods of time (e.g., 1 week, 1 month, 2 months), the X-bar stopcock 100 is designed as a lightweight valve mechanism that will remain relatively comfortable for the patient 502. Furthermore, medical professionals need to regularly check and adjust the valve configurations of the X-bar stopcock 100 (e.g., every 4 hours, 6 hours, 8 hours, 12 hours), and the placement on the patient's shoulder provides easy access to manipulate the X-bar stopcock 100.

The diagram 500 further includes at least one bag of saline. As illustrated, a first bag of saline 532 in fluid communication with the seventh port 136 via a first saline line 534. Additionally, a second bag of saline 536 is in fluid communication with a transducer 538 via saline line 540 and, indirectly, the third port 116 via saline line 542. The transducer 538 is capable of transmitting data to a monitor 544, such as, pressure data.

Furthermore, the X-bar stopcock 100 can be used to draw blood for testing. For example, a syringe 550 can be connected to the sixth port 134. The configuration of the bidirectional stopcock 102 and the three-way stopcock 104 for drawing blood is shown in greater detail in FIG. 7*c*. However, referring back to FIG. 5, the syringe 550 may be any known syringe capable of connecting with the sixth port 134. In some examples, the end of the syringe may include a luer lock or be configured to be secured to a luer lock.

Additionally, the bidirectional stopcock 102 may include color coded ports. For example, second port 114 may include a blue coloring to assist a medical practitioner in connecting the blue lumen 522 to the second port 114. Additionally or alternatively, the fourth port 118 may include a yellow coloring to assist a medical practitioner in connecting the yellow lumen 524 to the fourth port 118. As a result, the coloring of at least the second and fourth ports 114 and 118, decreases the time to connect the X-bar stopcock 100 and reduces chances of incorrectly connecting the X-bar stopcock 100 to the Swan-Ganz catheter.

Figure 6:
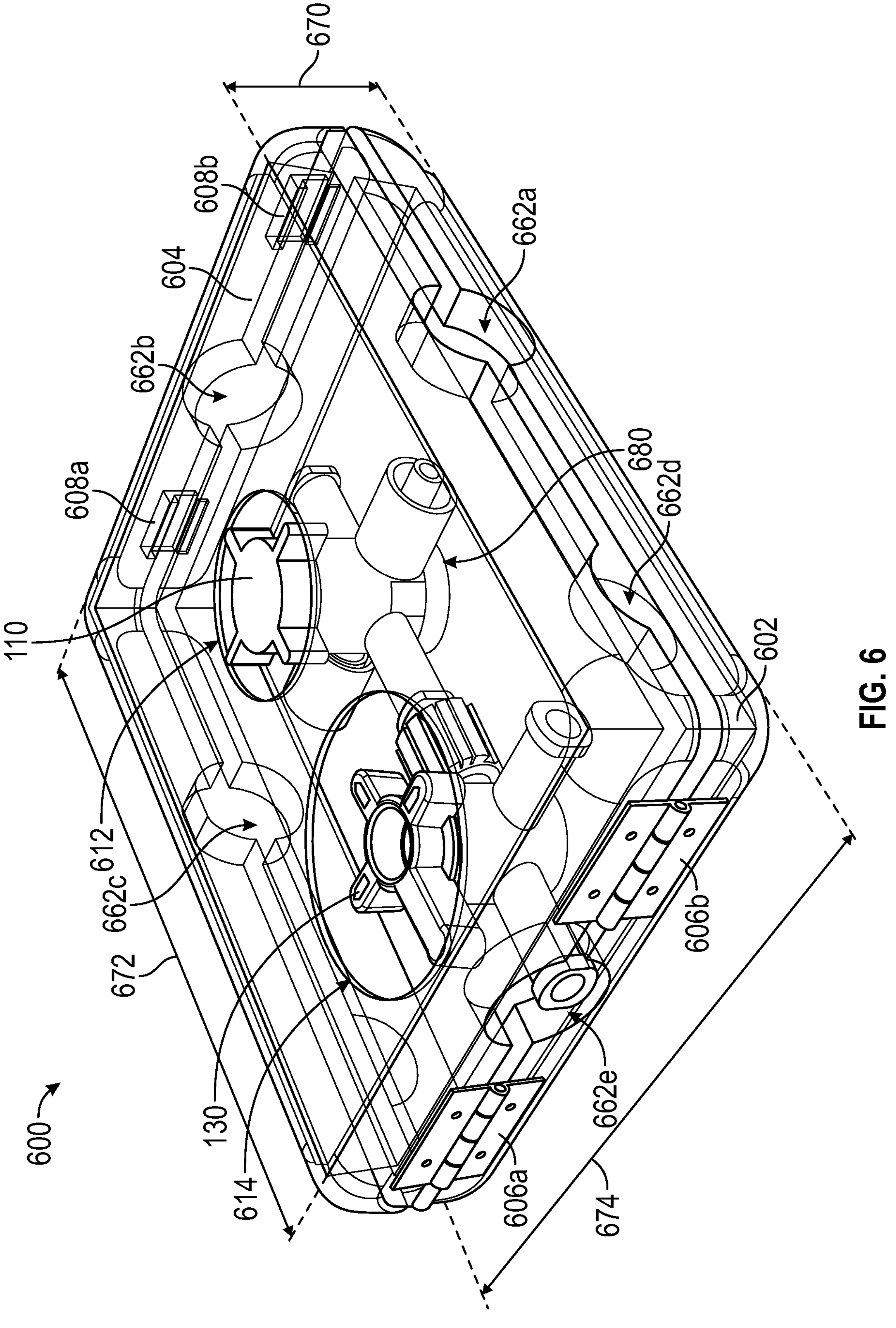
FIG. 6 is a perspective view of the X-bar stopcock for pulmonary artery catheterization disposed in a protective case, in accordance with the teachings of this disclosure.

FIG. 6 illustrates the X-bar protective case 600 in accordance with the teachings of this disclosure. The protective case 600 includes a bottom compartment 602, a top compartment 604, a first hinge 606*a* and a second hinge 606*b*, and a first latch 608*a* and a second latch 608*b*. In alternative embodiments, the hinges 606*a* and 606*b*, can be a latching mechanism to removably secure the top compartment 604 to the bottom compartment 602. Furthermore, the protective case 600 may be made of a transparent or slightly tinted material. As a result, a medical practitioner is able to visual inspect the X-bar stopcock 100 and all fluid connections, while protecting the integrity and desired positioning of the handle elements of the X-bar stopcock 100 disposed in the protective case 600.

Further, the protective case 600 may include a plurality of apertures and orifices. In various examples, the protective case 600 is made of various medical grade materials, and preferably clear (e.g., transparent) or lightly tinted materials. A clear or slightly tinted protective case 600 allows a medical professional to quickly visually inspect the fluid connections of the X-bar stopcock 100 without opening the protective case 600. As illustrated, the top compartment 604 includes a first aperture 612 and a second aperture 614. The bi-directional handle element 110 is accessible through the first aperture 612 and the three-way handle element 130 is accessible through the second aperture 614.

Further, the protective case 600 may further include at least five orifices 662*a*, 662*b*, 662*c*, 662*d*, and 662*e*. As illustrated, each orifice may correspond to a port on the X-bar stopcock 100, in which a fluid connection can pass through the protective case 600 and connect to the X-bar stopcock 100. As shown, the first orifice 662*a* corresponds to the second port 114; the second orifice 662*b* corresponds to the third port 116; the third orifice 662*c* corresponds to the fourth port 118; the fourth orifice 662*d* corresponds to the sixth port 134; and the fifth orifice 662*e* corresponds to the seventh port 136. Accordingly, and in view of FIGS. 5 and 6, the blue lumen 522 can pass through the first orifice 662*a* to connect to the second port 114 and the yellow lumen 524 can pass through the third orifice 662*c* to connect to the fourth port 118. Similarly, saline line 542 can pass through the second orifice 662*b* to connect to the third port 116 and the saline line 534 can pass through the fifth orifice 662*e* to connect to the seventh port 136. Lastly, the fourth orifice 662*d* is configured to receive a syringe to take a blood sample.

The protective case 600 is configured to increase patient comfort. In various examples, the protective case 600 may have a height 670 that is thin (e.g., approximately 0.5 inches to 1.5 inches). Additionally, the protective case may have a length 672 and a width 674. In various examples, the length can be between 2 inches and 4.5 inches and the width can be between 2 inches and 3.5 inches. In one preferred embodiment, the dimensions of the case are 3.9 inches in length, 3.1 inches in width, and 1 inch in height. As a result, the case is a compact case that additionally reduces the chance of the X-bar stopcock snagging on cords and tubes and increase patient comfort.

Medical professionals will assemble the X-bar stopcock 100 before or during a PAC procedure. For example, a medical professional will connect the bi-directional stopcock 102 to the three-way stopcock 104 via the first port 112 and fifth port 132 respectively. In other examples, the bi-directional stopcock 102 and the three-way stopcock 104 are made as a single unitary structure (e.g., a unified structure). When placing the X-bar stopcock 100 in the protective case 600, the X-bar stopcock 100 can be secured to the protective case 600. For example, the protective case 600 can include a securement mechanism 680. The securement mechanism 680 can include any form of circular latching mechanism. For example, the securement mechanism 680 can include a screw mechanism or a twist-off mechanism. As illustrated, the securement mechanism 680 could be a raised plastic aperture tightly fit to the X-bar stopcock to inhibit movement of the X-bar stopcock. Alternatively, the raised plastic aperture could loosely hold the X-bar stopcock to inhibit lateral movement and rely on the protective case 600 to prevent the X-bar stopcock to move vertically relative to the securement mechanism 680.

Figure 7A:
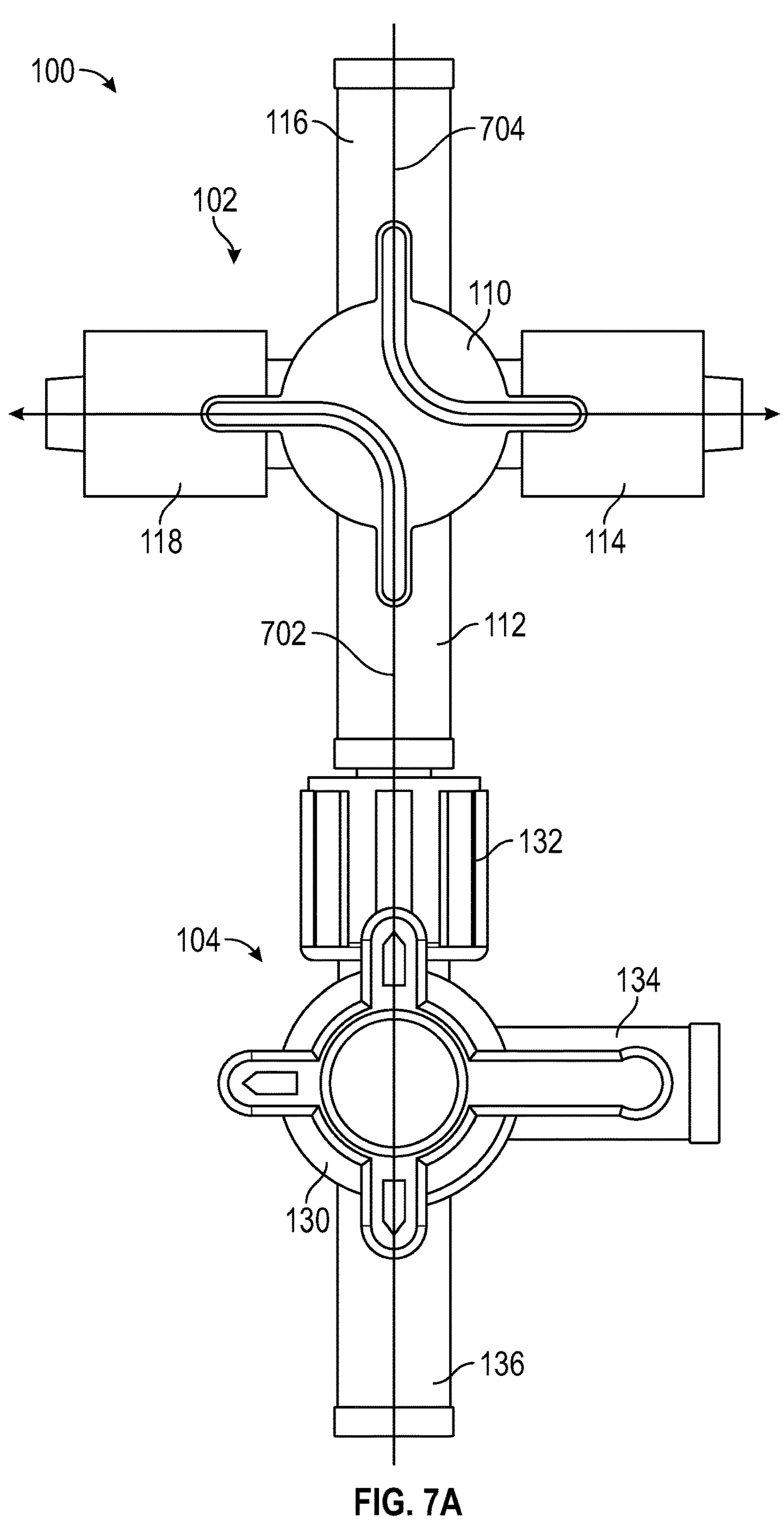
FIG. 7*a* is a first example configuration of the X-bar stopcock in accordance with the teachings of this disclosure.
Figure 7B:
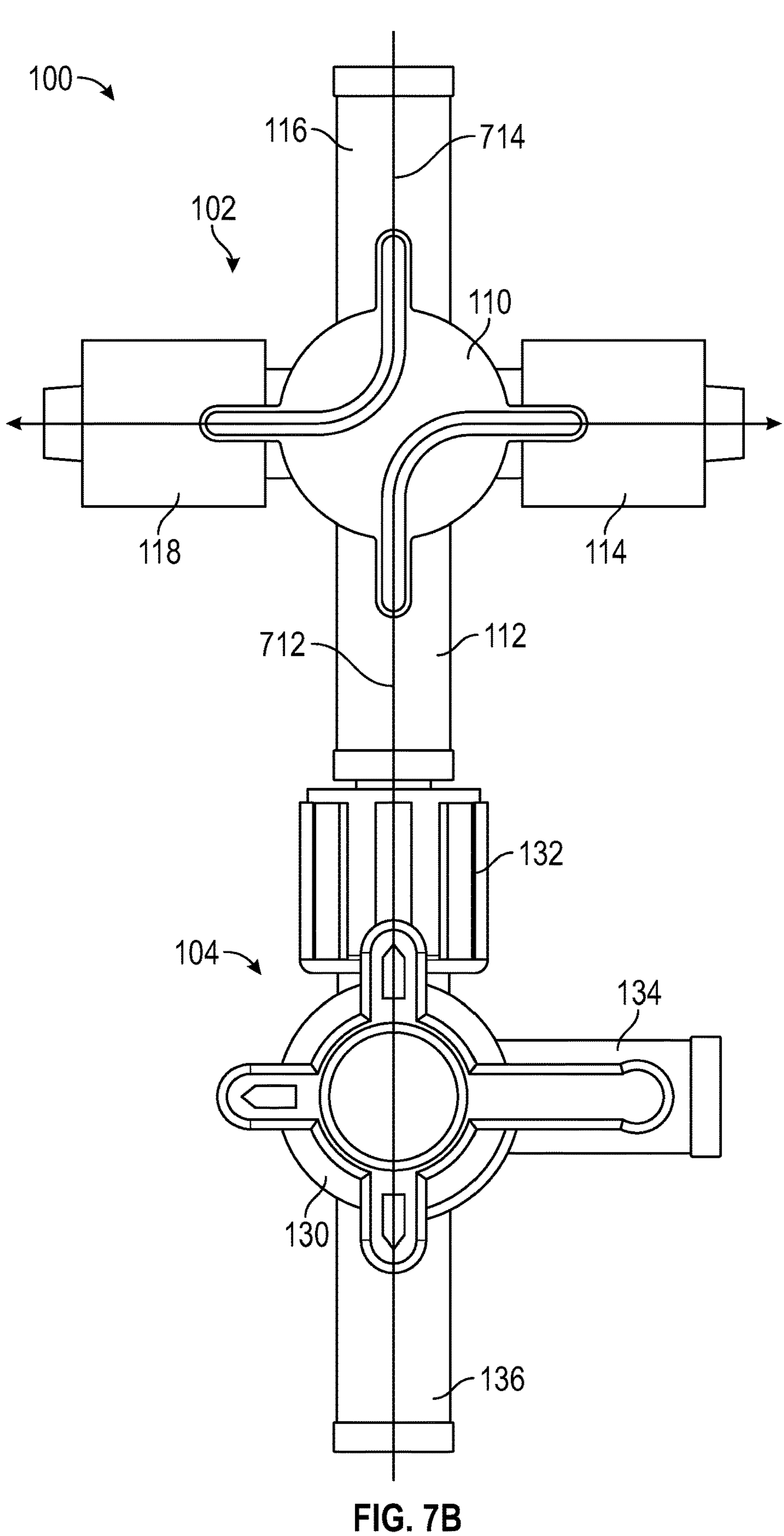
FIG. 7*b* is a second example configuration bar stopcock in accordance with the teachings of this disclosure.
Figure 7C:
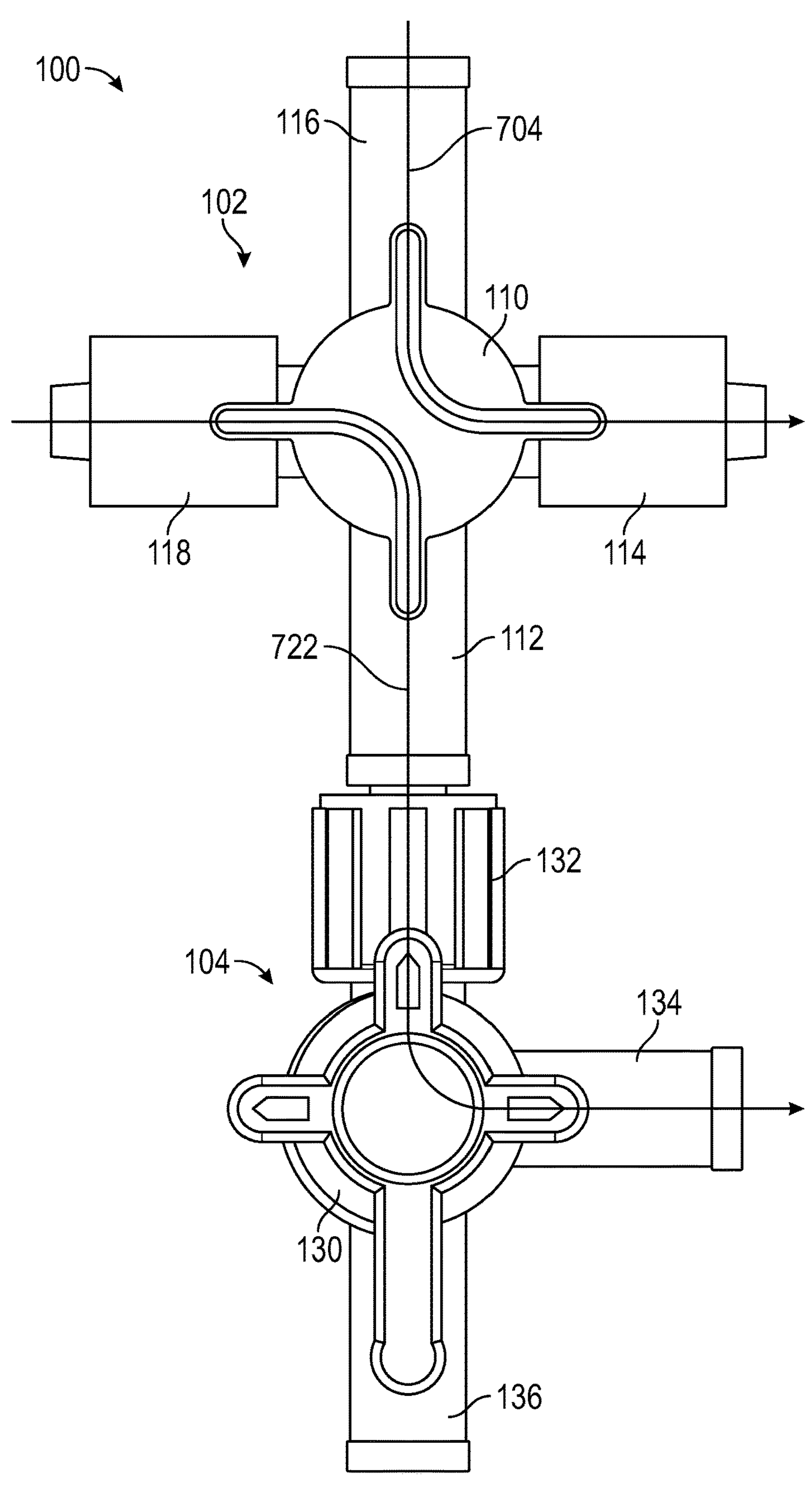
FIG. 7*c* is a third configuration bar stopcock in accordance with the teachings of this disclosure.

FIGS. 7*a*, 7*b*, and 7*c* illustrate example valve configurations of the X-bar stopcock 100 in accordance with the teachings of this disclosure. The illustrated combination of the bidirectional stopcock 102 and the three-way stopcock 104 can result in at least 10 different unique valve configurations. However, in a typical use of the X-bar stopcock 100, medical professionals will predominantly rely on three configurations, shown in FIGS. 7*a*, 7*b*, and 7*c*.

Turning to FIG. 7*a*, the X-bar stopcock 100 is configured to collect readings from the right atrium 512. As shown, the bidirectional stopcock 102 is in the second position and the three-way stopcock 104 is also in the second position. Accordingly, the first flow path 702 includes saline 532 flowing in through the seventh port 136 to the fourth port 118. Additionally, a second flow path 704 permits saline 536 to flow from the third port 116 to the second port 114. Because the transducer 538 is fluidly coupled to the third port 116 and the right atrium 512 is fluidly coupled to the second port 114 (as shown in FIG. 5), the transducer 538 can measure blood pressure in the right atrium 512.

Turning to FIG. 7*b*, the X-bar stopcock 100 is configured to collect readings from the pulmonary artery 514. As illustrated, the bidirectional stopcock 102 is in the first position and the three-way stopcock 104 is in the second position. Accordingly, the third flow path 712 includes saline 532 flowing in through the seventh port 136 to the second port 114. Additionally, the fourth flow path 714 permits saline 536 to flow from the third port 116 to the fourth port 118. Because the transducer 538 is fluidly coupled to the third port 116 and the pulmonary artery 514 is fluidly coupled to the fourth port 118 (as illustrated in FIG. 5), the transducer 538 can measure blood pressure in the pulmonary artery 514.

Turning to FIG. 7*c*, the X-bar stopcock 100 is configured to draw a blood sample from the pulmonary artery 514. As shown, the bidirectional stopcock 102 is in the second position and the three-way stopcock 104 is in the first position. Accordingly, the second flow path 704 permits saline 536 to flow from the third port 116 to the second port 114. Additionally, the fifth flow path 722 permits blood to flow from the fourth port 118 to the sixth port 134 when a syringe 550 is coupled to the sixth port 134.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A stopcock, comprising:

a bidirectional stopcock having a first port, second port, third port, and fourth port;

a three-way stopcock directly engaging the bidirectional stopcock and having a fifth port, sixth port, and seventh port; and a bidirectional handle element having a first position and a second position, wherein the bidirectional stopcock is fluidly coupled to the three-way stopcock via the first port and the fifth port, and wherein in the first position of the bidirectional handle element the first port and the second port are in fluid communication and the third port and the fourth port are in fluid communication, and in the second position the first port and the fourth port are in fluid communication and the second port and the third port are in fluid communication.

2. The stopcock of claim 1, wherein the second port and the fourth port are color coded.

3. The stopcock of claim 2, wherein the second port is coded with a first color and the fourth port is color coded with a second color, the first color being different from the second color.

4. The stopcock of claim 1, further comprising a three-way handle element.

5. The stopcock of claim 1, wherein the bidirectional stopcock is secured to the three-way stopcock.

6. The stopcock of claim 1, further comprising a protective case.

7. The stopcock of claim 6, wherein the protective case is transparent.

8. The stopcock of claim 6, wherein the protective case is lightly tinted.

9. The stopcock of claim 6, wherein at least one of the bidirectional stopcock and three-way stopcock are secured to the protective case.

10. The stopcock of claim 6, wherein the protective case includes a first aperture corresponding to the bidirectional handle element when the bidirectional stopcock is disposed in the protective case and a second aperture corresponding to the three-way handle element when the three-way stopcock is disposed in the case.

11. The stopcock of claim 1, wherein at least one of the first, second, third, fourth, fifth, sixth, and seventh ports comprises a luer lock.

12. A stopcock, comprising:

a bidirectional stopcock having a first port, second port, third port, and fourth port; and a three-way stopcock having a fifth port, sixth port, and seventh port, wherein, the bidirectional stopcock is fluidly coupled to the three-way stopcock via the first port and the fifth port, and a protective case including at least five orifices corresponding, respectively, to the second port, third port, fourth port, sixth port, and seventh port.

* * * * *